United States Patent [19]

Brix

[11] 4,055,897
[45] Nov. 1, 1977

[54] DENTAL ABRADING DEVICE AND METHOD

[75] Inventor: Charles J. Brix, Maplewood, Minn.

[73] Assignee: Minnesota Mining and Manufacturing Company, St. Paul, Minn.

[21] Appl. No.: 665,921

[22] Filed: Mar. 11, 1976

[51] Int. Cl.² .................. A61G 3/06; B24B 1/00; B24D 9/08

[52] U.S. Cl. ............................. 32/59; 51/328; 51/358; 51/401

[58] Field of Search ............ 51/358, 389, 378, 390, 51/394, 401, 407, 368, 328, 405; 32/59

[56] References Cited

U.S. PATENT DOCUMENTS

| | | | |
|---|---|---|---|
| 302,952 | 8/1884 | Smith | 51/378 |
| 336,695 | 2/1886 | Byers | 51/368 |
| 1,138,479 | 5/1915 | Hough | 51/407 |
| 1,506,078 | 8/1924 | Parks | 51/358 |
| 1,786,320 | 12/1930 | Stratford | 32/59 |
| 2,431,258 | 11/1947 | Kirchner | 51/407 |
| 2,531,775 | 11/1950 | Kenerson | 51/378 |
| 2,746,216 | 5/1956 | Hollingsworth | 51/358 |
| 2,842,844 | 7/1958 | Seal | 32/59 |
| 3,119,208 | 1/1964 | Gianatasio | 51/405 |
| 3,307,300 | 3/1967 | Field | 51/389 |
| 3,858,368 | 1/1975 | Cocherell | 51/358 |

*Primary Examiner*—Al Lawrence Smith
*Assistant Examiner*—Nicholas P. Godici
*Attorney, Agent, or Firm*—Cruzan Alexander; Donald M. Sell; James V. Lilly

[57] ABSTRACT

An abrading device comprising:

a conformable elastomeric disc-shaped body having a thickness in the range of from about 0.15 to 0.4 millimeters and a Shore A hardness in the range of from about 50 to 75; wherein said body is adapted to be connected to a driving means; and an exposed abrasive layer supported on said elastomeric body; wherein said abrasive layer has thickness in the range of less than about 0.3 millimeters and wherein the diameter of said abrasive layer is from about 1 to 1.1 times the diameter of said elastomeric disc-shaped body.

13 Claims, 6 Drawing Figures

DENTAL ABRADING DEVICE AND METHOD

FIELD OF THE INVENTION

This invention relates to abrading devices and processes for their utilization. More particularly it relates to such devices and processes useful in polishing various surfaces, such as surfaces comprising dental composite restorative resins.

Devices useful in polishing dental surfaces are known. Generally these devices comprise a disc having an abrasive material applied to a backing material such as paper, cloth, rubber, leather, celluloid, felt or polymeric film such as polyester film (e.g., see U.S. Pat. Nos. 302,952; 336,695; 1,138,479; 1,506,078; 2,431,258; 2,531,775; 3,119,208; and 3,858,368).

While these types of devices have been very useful in polishing metallic dental surfaces they have not been successful in polishing dental surfaces comprising dental composite restorative resins. These resins, or restoratives, such as those described in U.S. Pat. Nos. 3,452,437; 3,541,068; and 3,860,556, generally comprise a polymeric organic binder and finely divided, very hard, inorganic filler particles such as quartz. They are especially desirable in filling or repairing defects in the visible surfaces of anterior teeth because the color of the restorative resin can be closely matched to the color of the teeth. However, if such fillings are not polished they provide a rough surface which feels unpleasant to the patient and which is susceptible to staining. Polishing these restoratives has, however, proven to be extremely difficult.

Prior art devices have not proven successful in polishing these dental restoratives because they dislodge filler particles near the dental surface from the polymeric binder and thereby leave voids therein. Additionally these devices score or scratch the binder material. The voids and scratched areas are highly undesirable because the resulting surface is even rougher and more susceptible to staining than it was prior to the attempted polishing rather than being smooth and glossy or shiney and substantially free of voids or scratches as is characteristic of a well polished surface.

It has been discovered that the prior art devices do not polish the dental composite resins because they are not sufficiently elastic to permit the device to fully conform to the shape of the surface being polished nor do they limit the amount of pressure transmitted to the surface being polished. Consequently prior art polishing devices transmit too much pressure to the dental surface resulting in the above-described scratching and gouging.

Attempts by the operator to manually control the force exerted upon the dental surface being polished by the prior art devices have proven futile because it is virtually impossible to uniformly apply and maintain the low pressures necessary to successfully polish the dental composite resins. For these reasons it has been urged that dental composite resins cannot be polished by means of conventional polishing devices.

In an effort to provide a smooth surface on the filling a process was developed by others whereby the surface of the filling was formed against a smooth surface (e.g., matrix strip). However, such processes have not proven completely successful because the filling surface tends to be binder rich and, consequently, not durable. Moreover, it has proven difficult to fully cover the filling with the smooth surface because of the configuration of the teeth and the small area in which to work.

Another previous attempt to provide a smooth dental surface involved the application of a glaze coating over the filling surface. However, such surfaces typically have limited durability.

These deficiencies of the prior art have been overcome by the unique conformable abrading device of the present invention. It has been found that the novel device inherently controls the amount of pressure which is transmitted to the surface being polished without being substantially affected by increases in the pressure applied by the operator. This is accomplished by carefully balancing the thickness and hardness of the device. Consequently, dental composite restoratives can be polished to a surface that is substantially free from voids and scratches thus significantly reducing its susceptibility to staining. Moreover the devices of the invention allow the surface of filling to be uniformly abraded during polishing so that the finished surface comprises a uniform combination of binder and filler, thereby significantly improving the durability of the filling and also improving its stain resistance. The device of the invention accomplishes these results easily and without any increase in the time necessary to polish the fillings.

SUMMARY OF THE INVENTION

In accordance with the present invention there is provided an abrading device comprising:

a conformable, elastomeric, disc-shaped body having a thickness in the range of from about 0.15 to 0.4 millimeters and a Shore A hardness in the range of from about 50 to 75 wherein said body is adapted to be connected to a driving means; and an exposed abrasive layer supported on said elastomeric body; wherein said abrasive layer has a thickness of less than about 0.3 millimeters and wherein the diameter of said abrasive layer is from about 1 to 1.1 times the diameter of said elastomeric disc-shaped body.

In an alternative embodiment of the invention the abrasive layer has a diameter that is from about 1.1 to 1.3 times the diameter of the elastomeric disc-shaped body, and correspondingly the thickness of the elastomeric body is from about 0.3 to 0.7 millimeters and the Shore A hardness is from about 70 to 90.

Also provided herein is a process for polishing dental composite restoratives employing the above-described device.

DETAILED DESCRIPTION OF THE INVENTION

This invention is described in more detail hereinafter with reference to the accompanying drawings wherein like reference characters refer to the same parts throughout the several views and in which.

Figure 1:
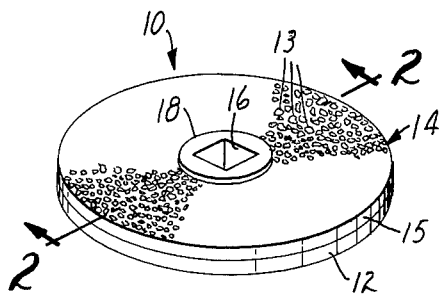
FIG. 1 shows a perspective view of a preferred embodiment of the invention.

Referring now to FIG. 1 there is shown a perspective view of a prefered embodiment of abrading device 10.

Device 10 comprises a comformable, elastomeric disc-shaped body 12 and an abrasive layer 14. Abrasive layer 14 comprises an abrasive material 13 and a substrate 15. An attachment means 16 for attaching device 10 to a driving means (e.g., a mandrel) is also provided. In the embodiment shown attachment means 16 comprises an opening through device 10. A hub 18 is provided around attachment means 16 and reinforces those portions of device 10 which define attachment means 16.

Disc-shaped body 12 comprises a conformable, elastomeric material. As it is used throughout this specification the phrase "elastomeric material" refers to a material that can be stretched at room temperature to at least twice its original length, and, after having been stretched and the stress removed, return with force to approximately its original length in a short time. This definition is contained in ASTM Special Technical Bulletin No. 184 (1956).

Disc-shaped body 12 has a thickness in the range of from about 0.15 to 0.4 millimeters and a Shore A hardness in the range of from about 50 to 75 (and preferably in the range of from about 60 to 65). Preferably body 12 has a thickness of about 0.25 millimeters when device 10 is to be utilized in the initial and intermediate steps of the polishing process and a thickness of about 0.15 millimeters when device 10 is to be utilized in the final step of the polishing process.

The conformability of the disc-shaped body 12 permits device 10 to essentially mate with the surface to be polished. Thus device 10 substantially conforms to all of the irregularities of said surface and thereby results in intimate contact between said surface and device 10. Consequently there is maximum contact between the device 10 and the surface to be polished.

The conformability of body 12 is the ability of device 10 to fill the irregularities of the surface to be polished and is measured by the hardness of disc shaped body 12. For purposes of this embodiment of the invention, body 12 has a Shore A hardness in the range of about 50 to 75. While the body 12 may have a Shore A hardness of less than about 50 it has been found that such devices are quite soft and accordingly require a relatively long polishing time in order to adequately polish the dental composite restoratives. On the other hand if the body 12 has a Shore A hardness of more than about 75, the device 10 loses its conformability and consequently scratches and gouges the surface rather than polishing it.

The amount of pressure transmitted normal to the surface to be polished is significantly affected by the thickness of body 12, although the conformability (e.g., hardness) also has an important effect. Thus, while body 12 may have a thickness of less than about 0.15 millimeters, devices 10 employing such a body 12 require long times in order to polish a dental surface. Consequently, they are not preferred. On the other hand, if body 12 is thicker than about 0.4 millimeters it loses its flexibility and transmits too much pressure to the surface to be polished.

Thus the balance of thickness and hardness is critical to the invention. It allows the user to exert sufficient force normal to the surface being polished so as to polish said surface while at the same time inherently limiting the maximum amount of force that can be exerted through device 10 normal to that surface to about 6 grams per square millimeter (so as to prevent the dental surface from being gouged or scratched). Moreover it allows device 10 to conform to the surface to be polished so as to maximize the polishing effect of the device. These results are achieved because as more pressure is exerted upon device 10 it deflects or bends to a greater degree, thereby transmitting most of the pressure along the axis of the shaft of the driving means while limiting the pressure applied normal to the surface to about 6 grams per square millimeter. Additionally, the area of contact between device 10 and the surface to be polished increases as the pressure upon device 10 increases thereby causing any increased pressure transmitted through device 10 to be spread over a larger area. This also helps to limit the pressure applied to the surface to a maximum of about 6 grams per square millimeter.

A variety of materials are useful as the conformable elastomeric body 12. Preferably they are resistant to moisture. Representative examples of useful elastomeric materials include pure gum rubber, polyurethane polymers, silicone polymers, polychloroprene polymers, vinyl polymers such as polyvinyl chloride, butadiene/acrylonitrile copolymers, etc.

A preferred elastomeric material comprises a crosslinked polyurethane such as that prepared by the polymerization of polyisocyanates (e.g., 2–4 and 2–6 toluenediisocyanate) with polyoxyalkylene glycols (e.g., polyoxypropylene glycol and polyoxyalkylene triol). A particularly preferred elastomeric material comprises the polymerization product of from about 8 to 10 parts by weight of a polyisocyanate having an isocyanate equivalent weight of from about 70 to 90 with from about 45 to 55 parts by weight of a polyoxyalkylene glycol having a number average molecular weight of from about 1000 to 2000 and a hydroxyl equivalent weight of from about 170 to 180. Other ingredients such as fillers, antioxidants, catalysts, etc., may also be added to the polymerization mixture. Typically these polymerizations are carried out at a slightly elevated temperature (e.g., 80° C). Preferably substantially all water has been removed from the ingredients.

Figure 2:
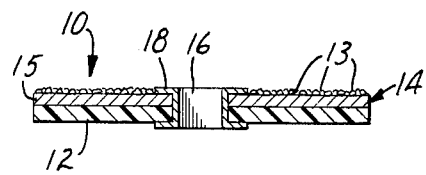
FIG. 2 shows a cross-sectional view of the device of FIG. 1 taken along the line 2—2.

Layer 14 comprises an abrasive material. The thickness of abrasive layer 14 may be varied provided that it be less than about 0.3 millimeters and that the combined thickness of body 12 and layer 14 be less than about 0.6 millimeters. Although the abrasive material of layer 14 may itself be supported directly upon body 12 it is typically applied to a substrate which is in turn supported upon body 12. Thus, as shown in FIG. 2, layer 14 comprises an abrasive material 13 applied to a substrate 15. In any event, it is preferred that abrasive layer 14 be unaffected by water.

When an abrasive layer 14 having these properties is supported upon an elastomeric body 12 having the above-described properties it provides an abrading device 10 having a thickness of less than about 0.6 millimeters and a Shore A hardness in the range of from about 50 to 75. Thus layer 14 does not significantly affect the physical properties or action of body 12. That is the device 10 is conformable and elastomeric and limits the amount of pressure that can be exerted through it to less than about 6 grams per square millimeter. The Shore A hardness of device 10 is measured by placing a disc 10, with its abrasive layer 14 up, upon a support block that is 7.5 centimeters in diameter by 6 millimeters in thickness. The block is chosen so as to have a Shore A hardness of from about 60 to 65. The disc 10 is then tested for Shore A hardness according to ASTM D-2240.

The size of the abrasive grit employed in layer 14 may be varied. However, it has been found that finer grit sizes (e.g., 50 micron maximum dimension or finer) are preferred for use during polishing. Representative examples of suitable abrasive materials include aluminum oxide, stannous oxide, garnet, silicone carbide, etc. Other abrasive materials may also be employed and will be obvious to those skilled in the art as a result of this disclosure. Although the color of the abrasive material is not critical to the invention, a lighter colored abrasive material is preferred since a darker colored abrasive material could cause discoloration of the surface to be polished. Thus, a particularly preferred abrasive material is aluminum oxide.

One type of abrasive layer that has been found particularly useful in the invention is "Production Paper, A-Weight, Wet-or-Dry" sandpaper commercially available from Minnesota Mining and Manufacturing Company. These materials comprise an abrasive material (e.g., aluminum oxide) and polymeric binder coated onto an "A" weight (i.e., 56 pound per ream), moisture resistant paper backing. The binder employed in the sandpaper is not critical to the present invention so long as they do not significantly affect the physical properties or the action of body 12. Suitable binders are known and include alkyds, phenolics, phenoxies, ureas and drying oils.

Attachment means 16 are provided in device 10. In the embodiment shown in FIGS. 1, 2, 4 and 5 means 16 comprises a rectangular opening through device 10. This permits the device to be utilized with commercially available driving means. Thus it may be employed with snap-on mandrels or with mandrels wherein the disc is attached by means of a screw. In any event it permits easy and rapid replacement of device 10. The opening may, however, have any of a variety of other geometric outlines. Thus, it may be specifically designed to be used with a particular mandrel.

Preferably a hub 18 is provided around attachment means 16. This construction is especially useful with snap-on mandrels. The hub reinforces the outer portions of the attachment means and assists in holding device 10 onto such mandrel. Hub 18 may be constructed from a variety of materials such as metal, plastics, etc. The size of hub 18 is not critical to the invention provided that it is large enough to be firmly anchored to device 10 while not being so large as to interfere with the operation of device 10.

Abrading device 10 may be provided in a variety of geometric shapes. Generally circular shapes are preferred so as to eliminate sharp corners which may cause difficulties during the polishing process and to maximize the area available for contact with a surface to be polished. Device 10 may also be provided in a variety of sizes. Commonly circular discs are from about one to two centimeters in diameter.

Abrading device 10 may be prepared by a variety of techniques. For example abrasive layer 14 may be easily applied to the material which is to comprise conformable elastomeric body 12 by simply coating a slurry of the abrasive material and a suitable binder thereon followed by drying. Alternatively a section of "Wet-or-Dry" sandpaper may be adhered to the material which is to comprise elastomeric body 12 by means of, for example, a pressure sensitive adhesive. In a preferred preparation, a mixture of polymerizable ingredients which are to comprise elastomeric body 12 is coated onto the back surface of abrasive layer 14. A variety of conventional coating techniques may be employed such as knife coating, curtain coating, etc. The mixture is then polymerized in situ by heating it to, for example, 80° C.

In any event the desired shape and size of device 10 may be cut from the resulting construction. Attachment means 16 may then be provided on device 10.

Figure 3:
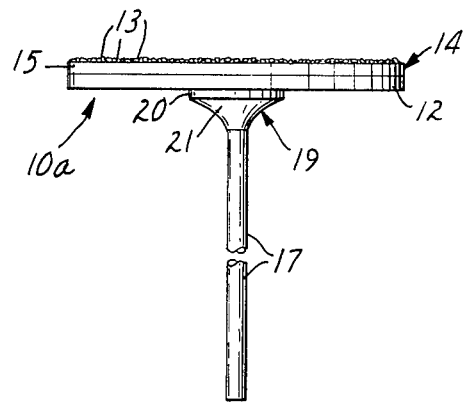
FIGS. 3 and 4 show alternative embodiments of the invention.
Figure 4:
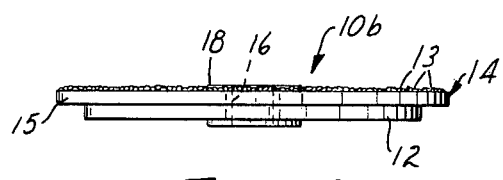

FIGS. 3 and 4 show alternative embodiments of the invention. In FIG. 3 device 10a is shown comprising abrasive layer 14 supported upon conformable, elastomeric body 12. A mandrel 17 is permanently affixed to layer 12 so that device 10a may be attached to a driving means. In this embodiment conformable elastomeric body 12 is molded around mandrel 17 at flange 19. Flange 19 comprises a circular portion 20 which narrows down to approximately the same diameter as that of mandrel 17 through shoulder 21.

In FIG. 4 device 10b is shown comprising an abrasive layer 14, a conformable elastomeric body 12, an attachment means 16 through device 10b and a hub 18. This embodiment differs from that shown in FIGS. 1 and 2 in that the thickness of elastomeric disc-shaped body 12 is from about 0.3 to 0.7 millimeters thick, the Shore A hardness is from about 70 to 90 while the diameter of abrasive layer 14 is from about 1.1 to 1.3 times the diameter of elastomeric body 12. As discussed previously the pressure transmitted to the dental surface is significantly affected by the thickness and conformability (as measured by the hardness) of the elastomeric disc-shaped body. However, in the embodiment shown in FIG. 4, the diameter of the abrasive layer 14 and body 12 also affect the amount of pressure transmitted to the dental surface. Thus in this embodiment the balance of thickness and hardness of the body 12, and the diameter of layer 14 is critical in order to obtain a device with the proper characteristics.

Figure 5:
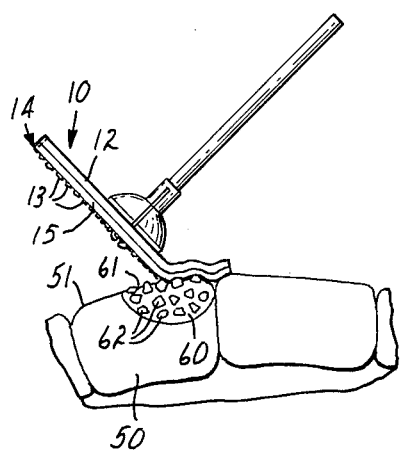
FIG. 5 shows a method of polishing dental composite restoratives utilizing the abrading device of the present invention.

FIG. 5 shows a method whereby dental composite restorative resins may be polished utilizing the abrading device of the invention. In this method a tooth 50 is provided that has a portion thereof filled with dental composite restorative 60. The exterior surface 61 of resin 60 is often raised above the exterior surface 51 of tooth 50. Additionally, filler particles 62 of resin 60 extend above surface 61.

To polish surface 61 an abrading device 10 is connected to a driving means (i.e., a mandrel) and a portion of surface 61 is contacted with the driven abrasive device 10. As can be seen by reference to the figure, the area of device 10 in contact with surfaces 51 and 61 conforms to the irregularities in said surfaces. Thus the area of contact is maximized and the polishing action of device 10 is applied to substantially the entire contacted surface. Several abrasive discs 10 having varying sizes of abrasive particles are preferably employed during the polishing process. For example, abrasive particles having a maximum dimension of about 50 microns is employed during a first or coarse polishing step, while abrasive particles having a maximum dimension of about 25 microns is employed during a second or intermediate polishing step and abrasive particles having a maximum dimension of about 15 microns is employed during a final or fine polishing step.

Figure 6:
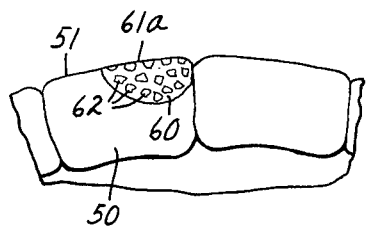
FIG. 6 shows the product obtained from the method of FIG. 5.

FIG. 6 shows the product obtained by following the above-described process. As can be seen, surface 61 has been polished so as to form surface 61a wherein substantially all of the filler particles 62 have been worn down so as to be flush with said surface without removing any of the filler from the composite itself. Additionally, said surface is in the same plane as that of surface 51. Consequently the polished composite surface is smooth and glossy and is substantially free of projections and voids.

The abrading device and method of polishing dental composite restoratives described in the specification and drawings represent but a few embodiments of the invention. Other embodiments are also possible as will be understood by those skilled in the art and are included within the scope of the claims set forth hereinafter.

The following examples are meant to further illustrate the invention without limiting it. All references to "parts" are references to parts by weight unless otherwise noted.

The surface smoothness produced by the varying polishing devices employed in the examples was measured by means of a "Proficorder Microrecorder" commercially available from Bendix Metrology Division of Bendix Corp. This device measures the vertical deflection of a stylus propelled across a surface, the stylus being propelled at a constant speed, and exerting a constant pressure upon the surface. The deflections of the stylus are caused by surface irregularities. Thus the more irregular (e.g., rough) the surface the higher the resultant reading. In each of the tests the stylus was 0.0025 millimeters in diameter, the pressure exerted by the stylus was one milligram, the travel speed of the stylus was 0.0125 millimeters per second, and the roughness width cut off was 0.075 millimeters.

EXAMPLE

Cured specimens of dental composite restorative (each 2 × 0.7 × 0.3 cm) were prepared from "Concise" brand dental restorative resin commercially available from Minnesota Mining and Manufacturing Company. "Concise" brand dental restorative resin comprises a polymeric organic binder and a finely divided, very hard inorganic filler.

Polishing discs (65 average Shore A hardness) according to the present invention were prepared. The discs each comprised a 16 millimeter diameter elastomeric disc-shaped body of crosslinked polyurethane and a 16 millimeter diameter abrasive layer having aluminum oxide as the abrasive.

The crosslinked polyurethane was prepared by mixing the following ingredients together:

| PART A | | |
|---|---|---|
| 2000 number average molecular weight polyoxypropylene glycol | 16 | parts by weight |
| 1500 number average molecular weight polyoxypropylene triol | 30 | parts by weight |
| Calcium Octoate | 0.3 | parts by weight |
| Attapulgus Clay | 45 | parts by weight |
| Methylene Bis(2,6 diethylaniline) (10% solution in polyoxypropylene glycol) | 1.5 | parts by weight |
| Titanium dioxide | 6 | parts by weight |
| Stannous Octoate | 0.6 | parts by weight |
| 2 Ethyl hexoic Acid | 0.6 | parts by weight |
| PART B | | |
| 2-4, 2-6 toluene diisocyanate (80/20 weight) | 9.3 | parts by weight |
| 2000 number average molecular weight polyoxypropylene glycol | 2.5 | parts by weight |
| 1500 number average molecular weight polyoxypropylene triol | 2.5 | parts by weight |

Parts A and B were blended together and coated onto the back side of the abrasive layer and allowed to polymerize in situ at about 85° C.

Separate discs having coarse, medium and fine abrasive particles thereon were prepared. The coarse disc was 0.44 millimeter thick and had abrasive particles thereon having a maximum dimension of about 40 microns. The medium disc was 0.37 millimeter thick and had abrasive particles thereon having a maximum dimension of about 21 microns. The fine disc was 0.32 millimeters thick and had abrasive particles thereon having a maximum dimension of about 1 to 3 microns. The abrasive layer of the coarse and medium polishing discs comprised "Wet-Or-Dry" sandpaper commercially available from Minnesota Mining and Manufacturing Company. The abrasive layer of the fine polishing disc comprised a backing of "A" weight (56 lbs. per ream) water proof paper to which a coating comprising a slurry of about 115 parts by weight aluminum oxide (1–3 micron size) and about 100 parts by weight phenoxy resin was applied. Square attachment means were provided through the center of the discs. A brass eyelet was provided to reinforce the attachment means.

Polishing discs (96 average Shore A hardness and 16 millimeter diameter) were also prepared. These discs were similar to commercially available polishing discs. Each disc had a 0.19 millimeter thick polyester backing and an abrasive layer of aluminum oxide. Separate coarse, medium and fine polishing discs were prepared. The coarse disc employed abrasive particles having a maximum dimension of 40 microns. The medium disc employed abrasive particles having a maximum dimension of 32 microns. The fine disc employed abrasive particles having a maximum dimension of 1–3 microns. A mixture of an epoxy resin binder and abrasive material was coated onto the polyester backing and dried to form the coarse and medium discs. The fine polishing disc was formed by laminating an abrasive layer comprising a backing of "A" weight (56 lbs. per ream) water proof paper to which a coating comprising a slurry of about 115 parts by weight of abrasive material and about 100 parts by weight of phenoxy resin had been applied to the polyester.

Individual specimens were polished with each of the discs and tested for surface smoothness on the "Proficorder" using the procedures previously described. Five specimens were polished with the discs and an arithmatic average of the surface smoothness was reported. In each case the first step in the polishing employed a polishing disc having abrasive particles having a maximum dimension of 100 microns and a 0.145 millimeter thick polyester backing. Such discs are commercially available from Zirc Company. The surface smoothness obtained after polishing with each disc of the invention is compared with the surface smoothness obtained with each of the polyester backed discs. The results are reported below in microinches of deflection.

| Size of Abrasive Employed During Polishing Steps (Microns) | Surface Smoothness (Microinches) | |
|---|---|---|
| | Disos of Invention | Polyester Backed Discs |
| 40 | 18 | 23 |
| 40 and 21 | 16 | 20 |
| 40 and 21 and 3 | 6 | 25 |

As can be seen the specimens polished with the discs of the invention provided smoother surfaces than specimens polished with the polyester backed discs. Additionally the process of employing successively finer polishing discs resulted in surfaces that were smooth and free of major irregularities when the discs of the invention were used while the surfaces polished with the polyester backed discs were rough and had major irregularities. Also the surfaces polished with the successively finer polyester backed discs did not exhibit the progressive improvement in surface smoothness that the surfaces polished with the successively finer discs of the invention did.

I claim:
1. An abrading device comprising:
   a conformable elastomeric disc-shaped body having a thickness in the range of from about 0.15 to 0.4 millimeters and a Shore A hardness in the range of from about 50 to 75; wherein said body is adapted to be connected to a driving means; and
   an exposed abrasive layer supported on said elastomeric body; wherein said abrasive layer has a thickness less than about 0.3 millimeters and wherein the diameter of said abrasive layer is from about 1 to 1.1 times the diameter of said elastomeric disc-shaped body.
2. A device according to claim 1 wherein said elastomeric disc-shaped body has a Shore A hardness in the range of from about 60 to 65.
3. A device according to claim 2 wherein said abrasive layer comprises an abrasive material supported on a paper substrate.
4. A device according to claim 3 wherein said abrasive material is aluminum oxide.
5. A device according to claim 4 wherein said aluminum oxide has a maximum dimension of about 15 microns.
6. A device according to claim 4 wherein said aluminum oxide has a maximum dimension of about 25 microns.
7. A device according to claim 4 wherein said aluminum oxide has a maximum dimension of about 50 microns.
8. A device according to claim 5 wherein said elastomeric disc shaped body comprises a crosslinked polyurethane prepared by the polymerization of from about 8 to 10 parts by weight of a polyisocyanate having an isocyanate equivalent weight of from about 70 to 90 with from about 45 to 55 parts by weight of a polyoxyalkylene glycol having a number average molecular weight of from about 1000 to 2000 and a hydroxyl equivalent weight of from about 170 to 180.
9. A device according to claim 1 wherein said elastomeric disc-shaped body and said abrasive layer are adapted to be connected to a driving means by means of an opening through each, wherein said opening has a reinforced periphery.
10. A device according to claim 1 wherein said body is permanently connected to a mandrel.
11. An abrading device comprising:
   a conformable elastomeric disc shaped body having a thickness of from about 0.3 to 0.7 millimeters and a Shore A hardness in the range of from about 70 to 90, wherein said body is adapted to be connected to a driving means; and
   an exposed abrasive layer supported on said elastomeric body, wherein said abrasive layer has a thickness less than about 0.3 millimeters and wherein the diameter of said abrasive layer is from about 1.1 to 1.3 times the diameter of said elastomeric disc shaped body.
12. A method for polishing a dental composite restorative comprising the steps of:
   providing an abrading device comprising (a) a conformable elastomeric disc-shaped body having a thickness in the range of from about 0.15 to 0.4 millimeters and a Shore A hardness in the range of from about 50 to 75; wherein said body is adapted to be connected to a driving means; and (b) an exposed abrasive layer supported on said elastomeric body; wherein said abrasive layer has a thickness less than about 0.3 millimeters and wherein the diameter of said abrasive layer is from about 1 to 1.1 times the diameter of said elastomeric disc-shaped body; and
   driving said abrading device by a driving means; and
   contacting said dental restorative with the exposed abrasive layer of said driven abrading device with a maximum force normal to said dental restorative of about 6 grams per square millimeter for a time sufficient to polish said restorative, wherein said abrading device limits the maximum amount of the force applied normal to said restorative to about 6 grams per square millimeter.
13. A method for polishing a dental composite restorative comprising the steps of:
   providing an abrading device comprising (a) a conformable elastomeric disc-shaped body having a thickness of from about 0.3 to 0.7 millimeters and a Shore A hardness in the range of from about 70 to 90, wherein said body is adapted to be connected to a driving means; and (b) an exposed abrasive layer supported on said elastomeric body, wherein said abrasive layer has a thickness less than about 0.3 millimeters and wherein the diameter of said abrasive layer is from about 1.1 to 1.3 times the diameter of said elastomeric disc-shaped body; and
   driving said abrading device by a driving means; and
   contacting said dental restorative with the exposed abrasive layer of said driven abrading device with a maximum force normal to said dental restorative of about 6 grams per square millimeter for a time sufficient to polish said restorative wherein said abrading device limits the maximum amount of the force applied normal to said restorative to about 6 grams per square millimeter.

* * * * *

UNITED STATES PATENT AND TRADEMARK OFFICE
CERTIFICATE OF CORRECTION

PATENT NO. : 4,055,897
DATED : November 1, 1977
INVENTOR(S) : Charles J. Brix

It is certified that error appears in the above-identified patent and that said Letters Patent are hereby corrected as shown below:

Col. 6, line 1, "in situ" should read -- *in situ* --.

Col. 7, line 65, "in situ" should read -- *in situ* --.

Col. 8, line 58, "Disos of" should read -- Discs of --.

Signed and Sealed this

Twenty-first Day of February 1978

[SEAL]

Attest:

RUTH C. MASON
*Attesting Officer*

LUTRELLE F. PARKER
*Acting Commissioner of Patents and Trademarks*